United States Patent

Campbell et al.

Patent Number: 5,840,148
Date of Patent: Nov. 24, 1998

[54] METHOD OF ASSEMBLY OF IMPLANTABLE TRANSPONDER

[75] Inventors: Neil E. Campbell, Hasbrouck Heights, N.J.; Donald J. Urbas, Evergreen, Colo.

[73] Assignee: Bio Medic Data Systems, Inc., Seaford, Del.

[21] Appl. No.: 497,480

[22] Filed: Jun. 30, 1995

[51] Int. Cl.⁶ .......................... B29C 69/02; B32B 31/06; B32B 7/00
[52] U.S. Cl. ............... 156/275.5; 156/69; 156/275.7; 156/293; 264/261; 264/263; 264/268; 264/272.11; 264/277; 264/494
[58] Field of Search ................ 264/494, 272.11, 264/267, 268, 272.13, 279.1, 271.1, 478, 496, 261, 263, 277; 156/275.7, 275.5, 69, 293

[56] References Cited

U.S. PATENT DOCUMENTS

| 2,300,495 | 11/1942 | Gerhart | 264/279.1 |
|---|---|---|---|
| 3,638,709 | 2/1972 | Brown, Jr. | 156/57 |
| 4,065,753 | 12/1977 | Paul, Jr. | |
| 4,073,835 | 2/1978 | Otsuki et al. | 264/22 |
| 4,142,383 | 3/1979 | Eberhart | 63/23 |
| 4,419,314 | 12/1983 | Bush | 364/130 |
| 4,470,858 | 9/1984 | McMaster | 156/103 |
| 4,753,704 | 6/1988 | Stewart | 156/275.5 |
| 5,025,550 | 6/1991 | Zirbes et al. | 29/605 |
| 5,074,318 | 12/1991 | Campbell et al. | 128/899 |
| 5,382,310 | 1/1995 | Ozimek et al. | 156/275.5 |
| 5,433,810 | 7/1995 | Abrams | 156/273.7 |
| 5,482,008 | 1/1996 | Stafford et al. | 119/174 |

FOREIGN PATENT DOCUMENTS

| 0 364 045 A1 | 4/1990 | European Pat. Off. |
| 230 923 | 8/1991 | New Zealand . |
| 260 514 | 5/1996 | New Zealand . |
| WO 93/05648 | 4/1993 | WIPO . |
| WO 95/17809 | 7/1995 | WIPO . |

*Primary Examiner*—Jan H. Silbaugh
*Assistant Examiner*—Suzanne E. Mason
*Attorney, Agent, or Firm*—Stroock & Stroock & Lavan LLP

[57] ABSTRACT

An improved identification marker and method of assembling the marker is provided, which includes the steps of providing a glass vial and filling the glass vial with a quick curing liquid to a predetermined volume corresponding to at least the volume wherein the unfilled volume of the vial is equal to the displacement volume of an IC circuit hybrid and antenna. The IC circuit hybrid and antenna are placed in the vial so as to be entirely enveloped by the liquid. A cap is placed on the vial and the liquid is cured. Preferably, the cap is an anti-migration cap so that when the transponder is implanted in an animal, it prevents the transponder from sliding out.

10 Claims, 2 Drawing Sheets

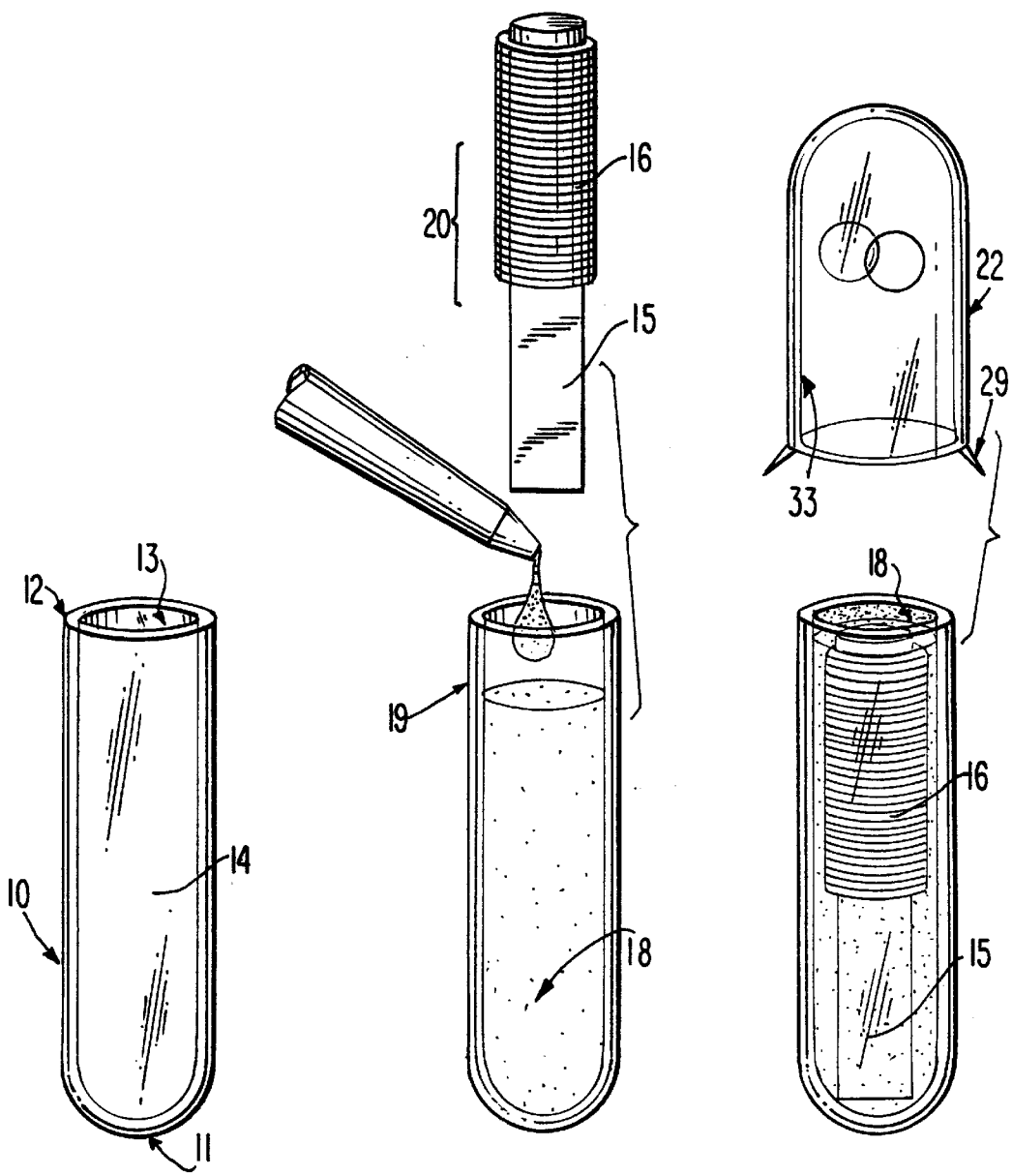

METHOD OF ASSEMBLY OF IMPLANTABLE TRANSPONDER

BACKGROUND OF THE INVENTION

This invention relates, in general, to an improved method of producing an identification marker that can be implanted and retained in an animal. Specifically, the identification marker is an implantable electric transponder containing identification information about the animal which can be read by an external detector.

An implantable electronic transponder containing identification information about an animal has significant utility in the biomedical field. For example, a programmable and temperature sensing electronic transponder, when implanted into an animal, makes possible not only the positive identification of the animal but also allows reading of the temperature of the animal.

One of the major requirements associated with the manufacture of an implantable transponder is the encapsulation of the IC circuit hybrid assembly and antenna coil, so that these critical components can be isolated from the body fluid, once the transponder is inserted into the animal. The body fluid contains a salt component that, when introduced into contact with the electronics of the transponder, will damage the electronics by corrosive action and render the electronics useless, usually within twenty four hours after injection. The encapsulation method must also be bio-compatible and completely non-adverse to the surrounding tissue at implant site.

Current methods of encapsulation use a glass capsule. Glass is heated and drawn to a precise dimension and cut to a length with one end open and the other end sealed, creating a vial. The IC circuit hybrid assembly and antenna coil are placed inside the glass vial. Once these components are placed in the glass vial, the open end of the glass vial is sealed. Methods currently available for sealing the open end have been limited to those using flame-and-polish and/or laser technology. Both of these methods are very time consuming and very expensive requiring elaborate tolerance control, special equipment and dedicated trained operators. Furthermore, laser technology is potentially very dangerous to an operator and special rooms and controlled environments must be established to utilize such methods.

An additional problem associated with the known methods for sealing the open end of the glass vial is the thermal shock that occurs to the delicate IC circuit hybrid assembly and antenna coil during manufacture as a result of the use of heat to seal the open end of the vial. Thermal shock can shorten the life of the unit and/or destroy the unit in production. To avoid this problem it is known to partially use glue to fix the components inside the vial before the open end of the vial is sealed.

The currently available methods for sealing the open end prevent a complete secondary seal of these critical components inside the vial utilizing glue. A material useful for gluing the electronic components inside the vial to provide a secondary seal (glue encapsulation isolation substrate) can only partially fill the vial, because the glue must be maintained away from the end of the vial, so that vial can be sealed. If glue is permitted near the end of the vial, the glue will contaminate the glass walls leading to combustion of the glue during heat treating, preventing a complete seal or in certain circumstances destroying the entire transponder assembly. This inability to form a secondary seal with the glue which completely covers the transponder by filling the vial renders the internal electronic components vulnerable to premature failure due to excessive vibration during shipment as well as body fluid damage, should the glass vial crack or break when placed inside the host animal.

An additional problem with the known sealing methods is that vial length must be longer to provide the additional glass wall material which is heated to cause a collapse upon itself, creating a glass ball or cap closure at the end of the vial. This results in the final assembly of the glass taking longer than necessary and works as a major disadvantage when the transponder must be placed in animals of any kind.

Furthermore, when currently known sealing methods are used, micron sized voids or bubbles will remain in the sealed end of the vial. These voids and bubbles are extremely difficult to detect because of the size of the transponder. When these unwanted voids remain, the body fluid will leak into the electronic assembly of the transponder and cause damage to it. Because heating of the glass is directly related to wall thickness, a cold forming or weld of the glass results. During shipment, the ball or cap end of the vial breaks off and makes the product useless for the intended application. Accordingly, a new transponder assembly and method for manufacturing a transponder assembly which protects the components within the glass vial without using heat, to overcome the shortcomings of the prior art, is desired.

SUMMARY OF THE INVENTION

A method for forming a marker includes the steps of providing a glass vial. The glass vial is filled with a quick curing liquid to a predetermined volume corresponding to at least the volume wherein the unfilled volume of the vial is equal to the displacement volume of an IC chip hybrid and antenna ("transponder components"). The transponder components are placed in the vial so as to be entirely enveloped by the curing liquid. A cap is placed on the vial and the liquid is cured. By reason of the curing, an improved transponder having an antimigration cap, having no voids, and in which the transponder components are securely maintained is provided.

Accordingly, it is an object of the invention to provide an improved method for manufacturing a transponder.

It is another object of the invention to provide a method for manufacturing a transponder which does not require heat.

Yet another object of the invention is to provide a method for manufacturing a transponder which produces a more stable transponder.

Still another object of the invention is to provide an improved transponder assembly in which the transponder components are isolated from body fluids and the like in use.

Still other objects and advantages of the invention will in part be obvious and will in part be apparent from the specification.

The invention accordingly comprises the several steps and the relation of one or more of such steps with respect to each of the others, the apparatus embodying features of construction, combination and arrangement of parts which are adapted to effect such steps, and the article which possesses the characteristics, properties and relation of elements, all as exemplified in the detailed disclosure hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view showing a vial used in accordance with the invention;

FIG. 2 is an exploded perspective view of the invention showing the IC chip hybrid and antenna just prior to insertion into a vial showing a step in accordance with the method of the invention;

FIG. 3 is an exploded perspective view of the cap and vial showing another step in accordance with the method of the invention;

DETAILED DESCRIPTION OF THE PREFERRED EMBODIMENTS

Figure 4:
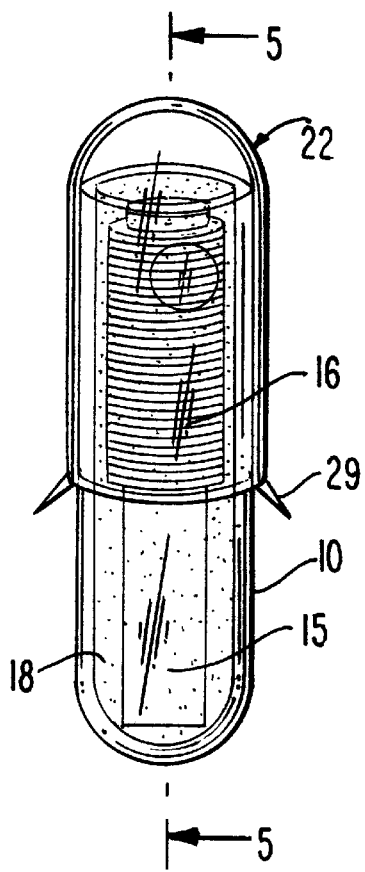
FIG. 4 is a perspective view of a transponder constructed in accordance with the invention.

An improved method of constructing an improved identification marker adapted to be implanted in an animal is provided in accordance with preferred embodiments of the invention and will be described with reference to FIGS. 1–5.

FIG. 1 generally shows a bio-compatible glass vial 10, having a completely sealed end 11 and an open end 12. Flame and polish methods, known in the art, can be used to produce sealed end 11 and also to slightly flame polish open end 12 to remove any sharp edges remaining from the cutting procedure used to make the glass vial 10. Glass vial 10 has an outer wall 14 and an inner wall 13.

FIG. 2 describes the next step of the assembly which comprises filling glass vial 10 with a quick hardening liquid. In an exemplary embodiment, a bio-compatible, UV curable material 18 in a liquid state is filled to a predetermined level 19. The predetermined level is selected so that when a transponder unit 20 is introduced into glass vial 10, UV curable material 18 is displaced and completely fills vial 10 and completely envelopes transponder unit 20. One such UV curable material 18 is a UV curing polyvinyl chloride bonding adhesive, one such as USP class 6 medical grade because of its suitability to animal usage. However, other quick curing materials may also be used for non-biomedical uses.

Transponder unit 20 can be comprised of an IC circuit hybrid assembly 15 and an antenna coil 16. Furthermore, transponder unit 20, in addition to containing identification information, can also be programmed to collect physiological data concerning the animal. For example, a transponder which is programmable and temperature sensing can be used to obtain the temperature of the animal.

As is depicted in FIG. 3, after transponder unit 20 is placed within glass vial 10, the UV curable material 18 completely envelopes transponder unit 20 and completely fills up glass vial 10, an anti-migration cap 22 is placed over the open end 12 of glass vial 10. The use of an anti-migration cap to assist in maintaining the transponder in a cannula and/or to prevent migration of the transponder from an animal after injection is described in detail in U.S. Pat. No. 5,074,318, which patent is incorporated herein by reference as if fully set forth herein. In one embodiment, when transponder unit 20 is placed in glass vial 10, UV curable material 18 brims over glass vial 10 and runs down outer wall 14, resulting in UV curable material 18 being present on the outer wall 14 of glass vial 10. Accordingly, when cap 22 is positioned on vial 10, the UV curable material will be disposed between the cap and the vial and will act as an adhesive securing the cap to the vial when the UV material is cured. Where there is no run over of UV curable material, a small amount of glue may be placed on the outer wall of vial 10 corresponding to the placement of cap 22 to glue cap 22 to vial 10.

Once placed over glass vial 10, anti-migration cap 22 will cover approximately one-half of glass vial 10. Anti-migration cap 22 serves to prevent the marker from sliding out of the animal, when the marker is implanted in the animal. Anti-migration cap 22 is made of a material having high coefficient of friction. Preferably, anti-migration cap is made of a bio-compatible material. For example, anti-migration cap 22 can be made by injecting medical grade polypropylene into a mold cavity. Further description of the anti-migration cap, as well as advantages provided by such device, is provided in U.S. Pat. No. 5,074,318.

After anti-migration cap 22 has been placed on glass vial 10, the unit is then UV irradiated for several seconds, resulting in UV curable material 18 turning from a liquid state into a solid mass. As a consequence of the irradiation, the UV curable material 18 in glass vial 10 turns into a solid mass, and the UV curable material 18 that has spilled over glass vial 10 and is trapped in the space between inner wall 33 of anti-migration cap 22 and outer wall 14 of glass vial 10 also solidifies, resulting in anti-migration cap 22 being permanently bonded to glass wall 13.

Figure 5:
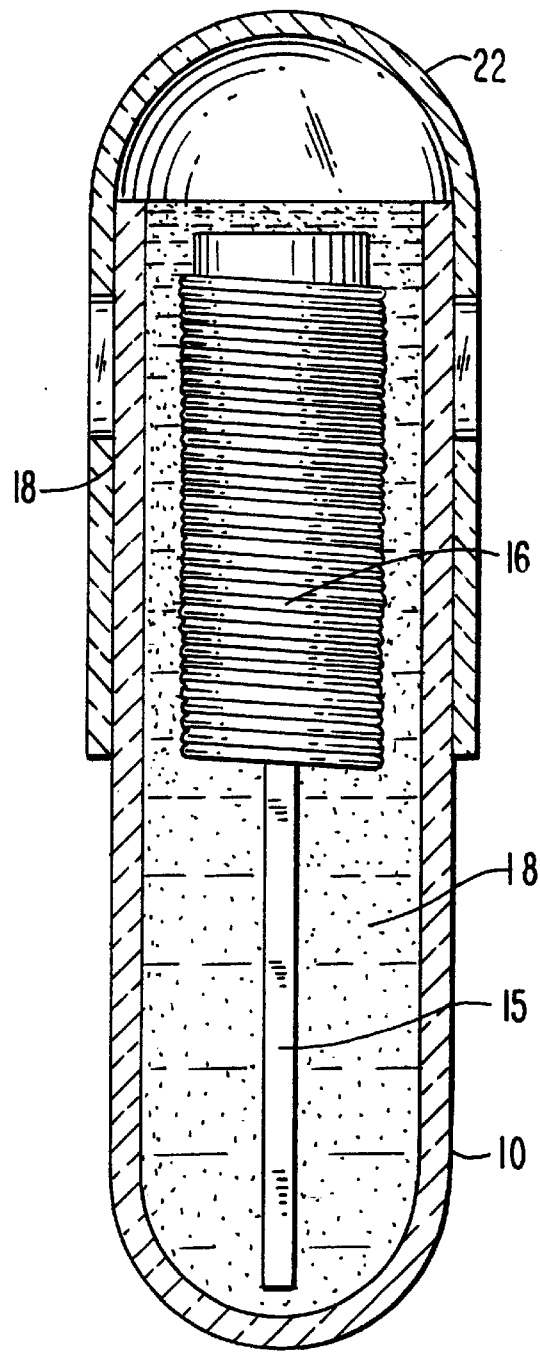
FIG. 5 is a sectional view taken along line 5—5.

When curable material 18 is cured to a hardened state, the result is a solid transponder having a glass case, the circuitry and antenna being extended and protected within the now solid cured material 18 as shown in FIGS. 4 and 5. The resulting transponder includes an outer glass layer 10, a solid protective layer 18, circuit 15 and antenna 16. Cap 22 acts as a partial coating of glass vial 10.

In an alternative embodiment, anti-migration cap 22 can also contain projections 29 to further prevent migration. Projections 29 are useful once the marker, an implantable transponder, is fully constructed and ready to be inserted into an animal. Usually the implantable transponder is inserted into an animal using an implanting apparatus, which is also described in U.S. Pat. No. 5,074,318. Projections 29 are used to interact with animal tissue after injection, preventing the marker from migrating.

In an embodiment of the implantable transponder to be used in mice studies or for pets, the dimensions of glass vial 10 are as follows: outer diameter of 2.12±0.03 mm, inner diameter of 1.75±0.03 mm and length of 13.20±0.3 mm. In such a case, it is preferred that transponder 20, when placed within glass vial 10, is located 0.02 mm below open end 12 of glass vial 10.

The marker thus produced is characterized by several distinct advantages over the implantable transponders made in accordance with the methods currently available in the art. For example, the anti-migration cap provides a means to create a smooth radius to the flat end of the glass vial. Furthermore, the anti-migration device is no longer a slip fit onto the glass but now is permanently bonded to the glass wall and is not likely to inadvertently slide off during shipment or use.

Also, the method disclosed herein eliminates the need to seal the open end of the glass vial using flame-and-polish or laser methodology. This elimination results in substantial cost savings, because special equipments and special trained operator required for these methods are no longer needed.

The thermal shock to the transponder unit is also eliminated, because no heat is required to seal the open end of the vial. The possibilities of voids or bubbles which might form when the open end of the vial is closed by the flame-and-polish and laser method are also eliminated.

The secondary seal provided to the transponder unit by the UV cured material also functions to isolate the electronics from the body fluid, even if the glass vial cracks or breaks during use in an animal, so that the damage that can result to the electronics is negligible.

Moreover, the complete encapsulation of the IC circuit hybrid and antenna coil assembly makes it very stable. This significantly improves the ability to program and calibrate the assembly since the very low mass of the device is very vulnerable and sensitive to changes in air or water temperature. By completely embodying the transponder assembly within the UV cured material, greater stability to the entire device is provided, creating one monolithic mass, which makes the necessary exercising of the programmable device much quicker and the calibration vastly improved for time and accuracy steps.

Furthermore, the secondary seal provided by UV cured material protects the electronics from vibration which occurs during shipment, significantly improving the survival rate of the shipped units.

Lastly, when this method is used, the length of the glass vial can be shorter than when using conventional methods, because the need to seal the open end of the vial using flame-and-polish or laser method is eliminated.

It will thus be seen that the objects set forth above, among those made apparent from the preceding description, are efficiently attained and, since certain changes may be made in carrying out the above method (process) and in the article set forth without departing from the spirit and scope of the invention, it is intended that all matter contained in the above description and shown in the accompanying drawing (s) shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of producing an identification marker formed from a vial, the method comprising the steps of:
    providing a vial having an open end and having an outer wall and an inner wall;
    partially filling the vial with a predetermined volume of curable material in a liquid state;
    inserting an electronic transponder into the vial containing the curable material, wherein the insertion of the electronic transponder results in the curable material completely enveloping the transponder;
    affixing a cap over the open end of the vial;
    curing the curable material; and
    assuring that the curable liquid material sufficiently fills the vial so that when the electronic transponder is inserted into the vial, the curable liquid material overflows the open end and covers, at least in part, the outer wall of the vial at the open end so that curing causes the curable liquid material disposed between the cap and the outer wall of the vial to bond the cap to the vial.

2. The method of claim 1, wherein the vial is a glass vial and further comprising the step of exposing the glass vial having the cap placed on the open end of the glass vial to UV irradiation for sufficient amount of time to solidify the UV curable material.

3. The method of claim 1, wherein the predetermined volume is at least as great as the volume of the vial minus the displacement volume of the transponder.

4. The method of claim 1, wherein the curable material comprises a UV curable polyvinyl chloride adhesive.

5. The method of claim 1, wherein the cap is an anti-migration cap which provides a smooth radius, when placed on top of the open end of the glass vial.

6. The method of claim 4, wherein the vial and the cap are bio-compatible.

7. The method of claim 1, wherein the transponder comprises an IC circuit hybrid assembly and an antenna coil.

8. The method of claim 1, wherein the transponder is programmable and capable of sensing the temperature of an animal.

9. The method of claim 1, wherein the cap is an antimigration cap.

10. A method of producing an identification marker formed from a vial, the method comprising the steps of:
    providing a vial having an open end and having an outer wall and an inner wall;
    partially filling the vial with a predetermined volume of curable material in a liquid state;
    inserting an electronic transponder into the vial containing the curable material, wherein the insertion of the electronic transponder results in the curable material completely enveloping the transponder;
    applying a glue to the vial to affix the cap to the vial;
    affixing a cap over the open end of the vial; and
    curing the curable material;
    wherein the predetermined volume is such that insertion of the transponder causes the curable material to spill out and run over the outer wall of the vial, so that the curable material will be disposed between the outer wall and the cap when the cap is affixed over the open end of the vial.

* * * * *